(12) United States Patent
Ehrenfels

(10) Patent No.: US 6,394,982 B1
(45) Date of Patent: May 28, 2002

(54) FIBRIN GLUE APPLICATOR SYSTEM

(75) Inventor: Karl Ehrenfels, Cheshire, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/495,007

(22) Filed: Jan. 31, 2000

Related U.S. Application Data

(60) Provisional application No. 60/052,253, filed on Jul. 11, 1997.

(51) Int. Cl.[7] .................................................. A61M 5/00
(52) U.S. Cl. ........................ 604/191; 604/187; 604/218; 604/213
(58) Field of Search ............................ 604/43, 61, 187, 604/191, 218

(56) References Cited

U.S. PATENT DOCUMENTS

| | | | |
|---|---|---|---|
| 1,948,388 A | 2/1934 | Liberson ..................... 128/234 |
| 2,112,160 A | 3/1938 | Johnson ...................... 128/234 |
| 3,223,083 A | 12/1965 | Cobey .......................... 128/92 |
| 3,236,418 A | 2/1966 | Dalle et al. .................. 222/135 |
| 3,467,096 A | 9/1969 | Horn .......................... 128/218 |
| 3,552,394 A | 1/1971 | Horn .......................... 728/218 |
| 3,767,085 A | 10/1973 | Cannon et al. ................ 222/82 |
| 4,040,420 A | 8/1977 | Speer ......................... 128/218 |
| 4,121,739 A | 10/1978 | Devaney et al. ............. 222/137 |
| 4,226,235 A | 10/1980 | Sarnoff et al. .............. 128/218 |
| 4,260,077 A | 4/1981 | Schroeder .................... 222/137 |
| 4,359,049 A | 11/1982 | Redl et al. .................. 128/218 |
| 4,465,476 A | 8/1984 | Gahwiler ..................... 604/191 |
| 4,631,055 A | 12/1986 | Redl et al. .................... 604/82 |
| 4,673,395 A | 6/1987 | Phillips ....................... 604/191 |
| 4,734,261 A | 3/1988 | Koizumi et al. .............. 422/100 |
| 4,735,616 A | 4/1988 | Eibl et al. ................... 604/191 |
| 4,826,048 A | 5/1989 | Skorka et al. ............... 222/137 |
| 4,874,368 A | 10/1989 | Miller et al. .................. 604/82 |
| 4,902,281 A | 2/1990 | Avoy ........................... 604/191 |
| 4,978,336 A | 12/1990 | Capozzi et al. ................ 604/82 |
| 4,979,942 A | 12/1990 | Wolf et al. .................... 604/83 |
| 5,116,315 A | 5/1992 | Capozzi et al. ................ 604/82 |
| 5,226,877 A | 7/1993 | Epstein ......................... 604/35 |
| 5,290,259 A | 3/1994 | Fischer ........................ 604/218 |
| 5,368,563 A | 11/1994 | Lonneman et al. ........... 604/82 |
| 5,376,079 A | 12/1994 | Hoim .......................... 604/191 |
| 5,409,465 A | 4/1995 | Boggs et al. ................. 604/191 |
| 5,464,396 A | 11/1995 | Barta et al. .................. 604/191 |
| 5,474,540 A | 12/1995 | Miller et al. ................. 604/191 |
| 5,505,704 A | 4/1996 | Pawelka et al. .............. 604/191 |
| 5,520,658 A | 5/1996 | Hoim .......................... 604/191 |
| 5,582,596 A | 12/1996 | Fukunaga et al. ........... 604/191 |
| 5,643,206 A | 7/1997 | Fischer ......................... 604/82 |
| 5,665,067 A | 9/1997 | Linder et al. .................. 604/82 |
| 5,740,965 A | 4/1998 | Miyagi et al. ............... 239/423 |

FOREIGN PATENT DOCUMENTS

| | | |
|---|---|---|
| EP | 0858776 | 8/1998 |
| WO | 9802098 | 1/1998 |
| WO | 9810703 | 3/1998 |
| WO | 9810704 | 3/1998 |
| WO | 9813094 | 4/1998 |
| WO | 9840115 | 9/1998 |

*Primary Examiner*—Gary Jackson

(57) ABSTRACT

A fibrin glue applicator system (10) is provided for dispensing a first and a second protein solution which form a biological adhesive when intermixed on an application site. The fibrin glue applicator system (10) includes a coupler interface (16), a disposable loading unit (DLU) (14), and a housing (12) having a handle portion (20) which includes a trigger (22) operatively associated with a slide bar (36) for dispensing the solutions from the DLU (14). Each piercer (66) is fluid communication with one of the two cylinders (46) of the DLU (14) via a respective conduit (64) connected to a respective main conduit (60). A first one-way valve (68) is included within each conduit (64) to open, and close a path leading from the piercer (66) to the main conduit (60). A second one-way valve (70) is fixed within each main conduit (60) in proximity to each dispensing orifice to open, and close a path leading from each cylinder (46) to its corresponding dispensing orifice.

18 Claims, 6 Drawing Sheets

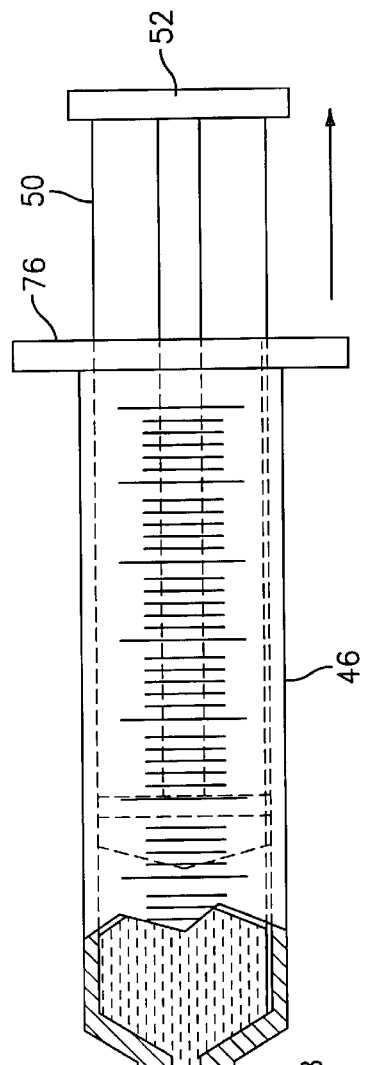
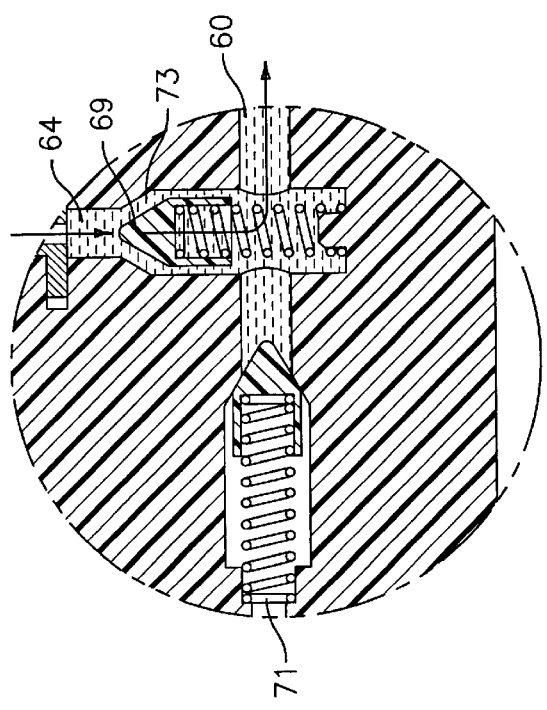
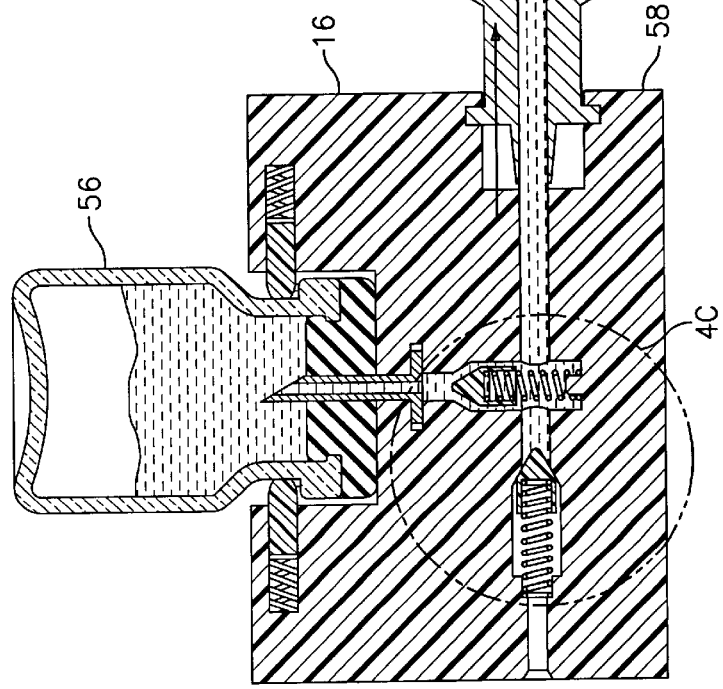
FIG. 4C
FIG. 4B

FIBRIN GLUE APPLICATOR SYSTEM

PRIORITY

This application claims priority to a U.S. Provisional Application filed on Jul. 11, 1997 having Application Ser. No. 60/052,253.

BACKGROUND

1. Technical Field

The disclosure relates generally to a fibrin glue applicator system for dispensing a first and a second component of a tissue sealant based on human or animal proteins and, more particularly, to an applicator system for dispensing a first and a second protein solution to be applied to tissues or organs to form a fibrin sealant for sealing wounds, stopping bleeding and the like.

2. Description of Related Art

A fibrin sealant is a biological adhesive formed by mixing two protein components, namely, fibrinogen and thrombin. Each protein component is derived from human plasma and is subjected to virus elimination procedures. The components are typically individually dehydrated and stored in separate vials as sterile freeze-dried powders.

It is known that purified fibrinogen and thrombin, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until applied at the application site. These protein solutions are generally mixed and dispensed by devices such as a dual syringe apparatus.

One dual syringe apparatus for applying a fibrinogen-based tissue adhesive is disclosed in U.S. Pat. No. 4,359,049 to Redl et al. This reference discloses a mechanism in which two standardized one-way syringes are held in a support having a common actuating means. The dispensing end of each syringe is inserted into a collection manifold where the two components are mixed. The components are then dispensed through a common needle capable of covering a limited area of the application site.

Typical devices for mixing and dispensing solutions of fibrinogen and thrombin require the addition of these proteins in powdered form to the body of the syringe. This makes the proteins susceptible to contamination by impurities which may enter the syringe body. Further still, the use of the syringe body to mix the proteins with water to create the protein solutions can cause the solutions to leak out from either the dispensing end of each syringe or the proximal end of the syringe body.

A dual syringe apparatus for the application of fibrinogen and thrombin solutions to an application site generally contains several parts, such as a syringe plunger, a "Y" manifold connector, a dispensing needle, a syringe holder, syringe needles, and conduits for transporting the solutions to the dispensing needle. Therefore, fibrin sealant applicators, such as disclosed in U.S. Pat. No. 4,359,049 to Redl et al. discussed above, and in U.S. Pat. No. 4,874,368 to Miller et al. and U.S. Pat. No. 4,979,942 to Wolf et al. are difficult to reuse. The replenishment of the protein components typically requires removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, adding sterile water to each syringe, replacing the syringe plunger, replacing the plunger clip, and mixing the solutions. In an application where time may be of the essence, such a lengthy replenishing process is impractical and cumbersome.

SUMMARY

A fibrin glue applicator system is provided for dispensing a first and a second protein solution. The first and second protein solutions form a biological adhesive when intermixed on an application site. The fibrin glue applicator system includes a coupler interface, a disposable loading unit (DLU), and a housing having a handle portion which includes a trigger operatively associated with a slide bar for dispensing the solutions from the DLU. The coupler interface is removably mounted to the DLU and the DLU is removably mounted to the housing.

The DLU includes two piston assemblies for storing the solutions therein before the solutions are dispensed. Each piston assembly includes a cylinder which matingly engages a piston having a rod which translates proximally and distally within the cylinder. The piston assemblies are connected to one another by a loading lever at a proximal end and a dispensing unit at a distal end for holding the assemblies substantially parallel to one another.

The coupler interface includes two mounting holes each having a piercer therein for receiving a vial having the first protein solution and a vial having the second protein solution. The protective seal on each vial is pierced by the piercer within each hole when the vials are inserted therein. Each piercer is in fluid communication with one of the cylinders of the DLU via a conduit connected to a main conduit. A first one-way valve is included within each conduit to open and close a path leading from the piercer to the main conduit. The first one-way valves are forced open by air pressure created when the loading lever connected to the two pistons of the DLU is translated proximally causing the protein solutions to be transferred to their corresponding cylinder.

When the protein solutions have been transferred from the vials to the cylinders of the DLU, the vials and the coupler interface can be removed from the DLU. The DLU is then mounted to the housing for dispensing the protein solutions from the cylinders to the application site.

The solutions are dispensed via two dispensing orifices each in fluid communication with one of the main conduits. A second one-way valve is fixed within each main conduit in proximity to each dispensing orifice to open and close a path leading from each cylinder to its corresponding dispensing orifice. The second one-way valves open when the solutions are forcibly transferred from the cylinders to the main conduits. The solutions are forcibly transferred when the pistons are translated distally by pressing the trigger of the handle portion to translate the slide bar distally which causes the loading lever to translate distally which in turn causes the pistons to translate distally thus creating pressure within the cylinders for dispensing the solutions within the main conduits. The first and second protein solutions are preferably fibrinogen and thrombin solutions which intermix on the application site to form a fibrin sealant.

BRIEF DESCRIPTION OF THE DRAWINGS

Various embodiments are described herein with reference to the drawings, wherein:

FIG. 4B is an enlarged cross-sectional view of the DLU and coupler interface with the dispensing valve in the closed position and the loading valve in the open position;

FIG. 4C is an enlarged view of the valves shown in FIG. 4B;

DETAILED DESCRIPTION OF PREFERRED EMBODIMENTS

Figure 1:
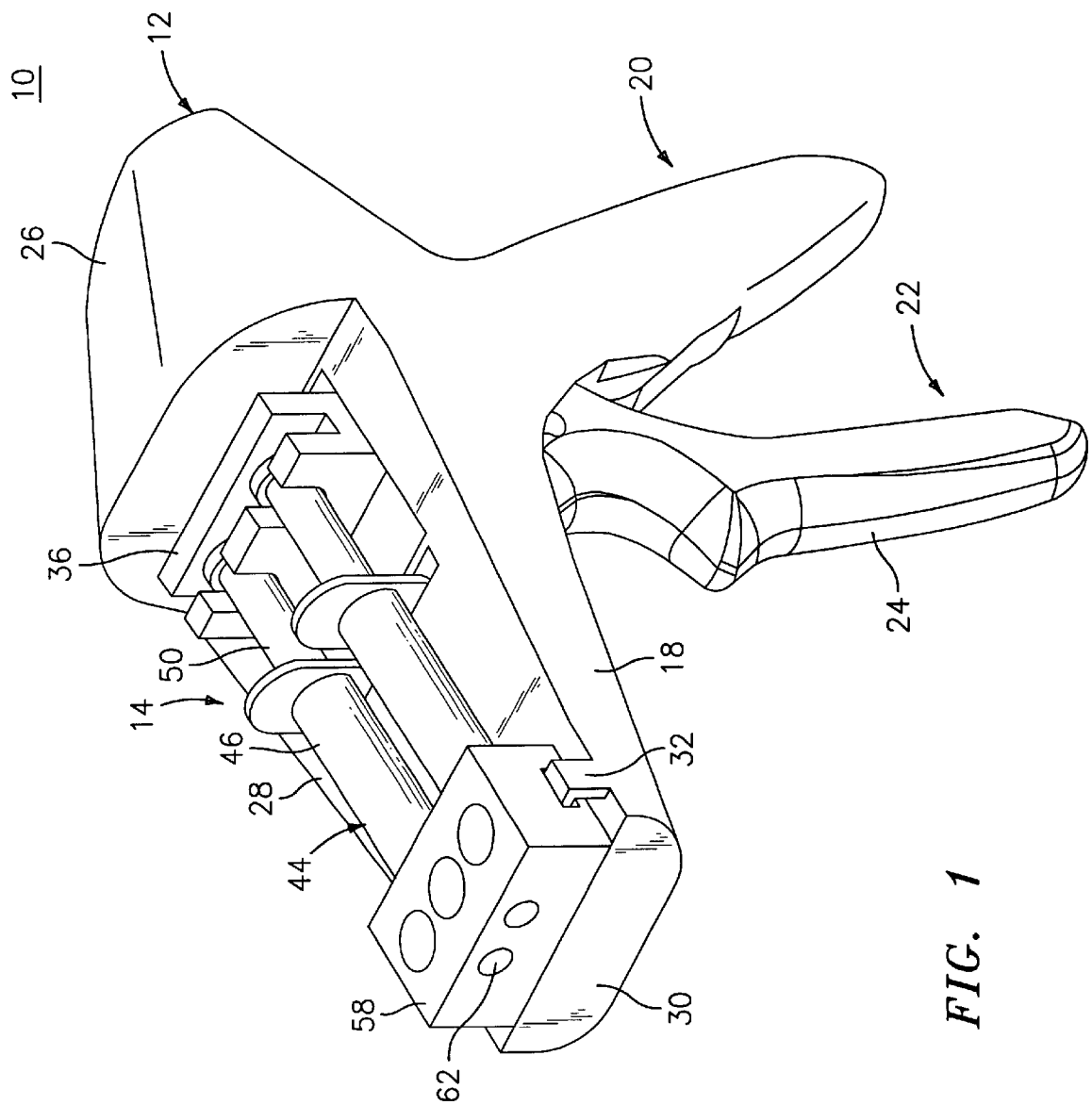
FIG. 1 is a perspective view of a preferred embodiment of a fibrin glue applicator system.
Figure 2:
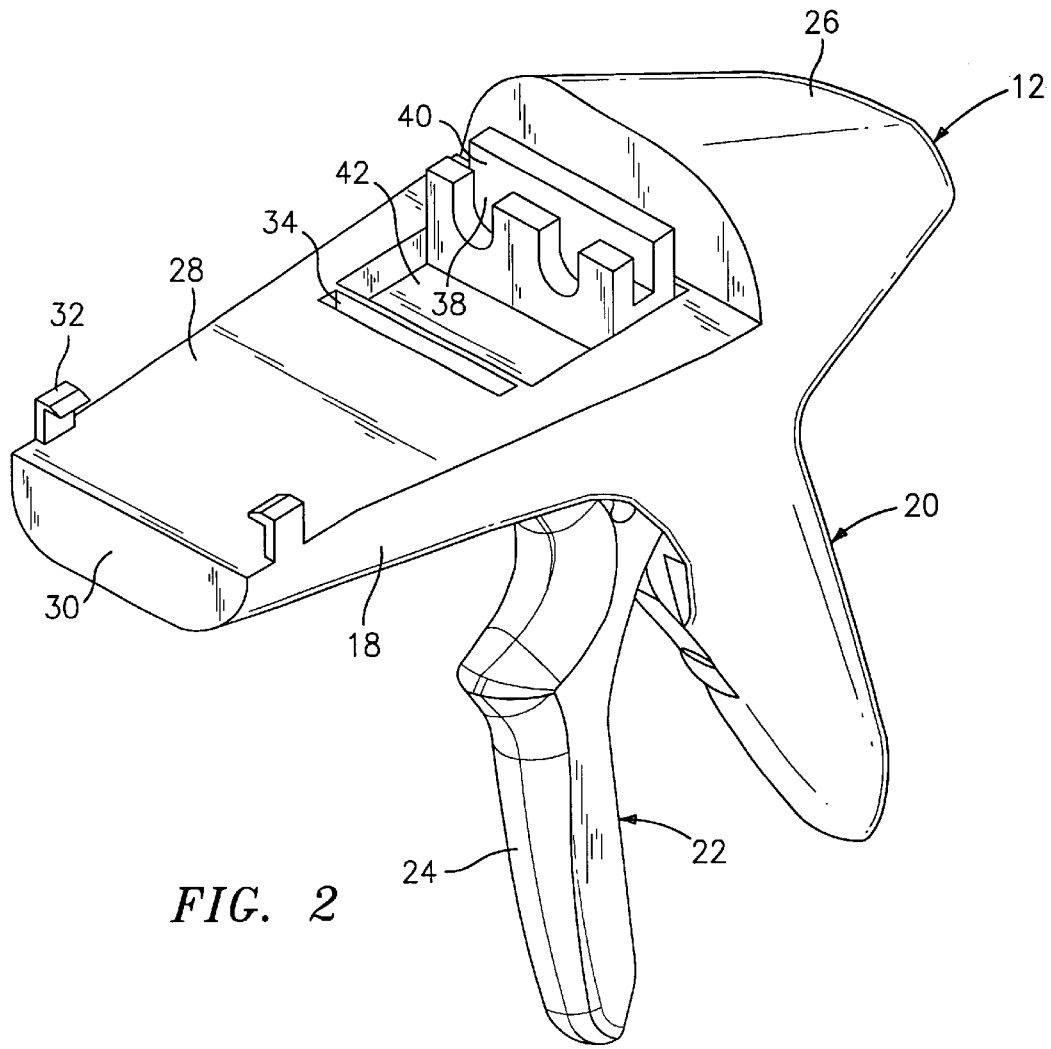
FIG. 2 is a perspective view of the housing showing the elongated body portion and handle portion.

Referring to FIGS. 1 through 4A, a fibrin glue applicator system and corresponding parts thereof according to a preferred embodiment of the present disclosure are shown. The applicator system, designated generally by numeral 10, includes a longitudinal housing 12, a disposable loading unit (DLU) 14, and a coupler interface 16. The housing includes an elongated body portion 18 defining a longitudinal axis and a handle portion 20.

The handle portion 20 includes a trigger 22 configured to pivot with respect to the handle portion 20. The trigger includes a grip portion 24 extending downwardly and adapted to be pressed by the fingers of a user's hand to actuate the applicator system 10 to dispense protein solutions within the DLU 14 as further described below.

The elongated body portion 18 includes a rounded proximal end 26 and a flat surface 28 extending from above the handle portion 20 to a distal end 30. A pair of flanges 32 extend perpendicular to the longitudinal axis at the distal end 30 and a slot 34 is formed at the mid-point of the elongated body portion 18.

Elongated body portion 18 further includes a slide bar 36 having two apertures 38 and a slot 40 adjacent thereto. The slide bar 36 is operatively associated with the trigger 22 for distal and proximal translation of the slide bar 36 along a chamber 42 of the elongated body portion 18 as the trigger 22 is moved proximally and distally, respectively. The trigger 22 may be operatively associated with the slide bar 36 by any conventional mechanism, such as a mechanism having rotatable gears and/or movable rods. It is contemplated to provide a ratchet mechanism having notches on an upper portion of the trigger 22 to control the amount of movement of the trigger 22 and hence the slide bar 36.

Figure 3:
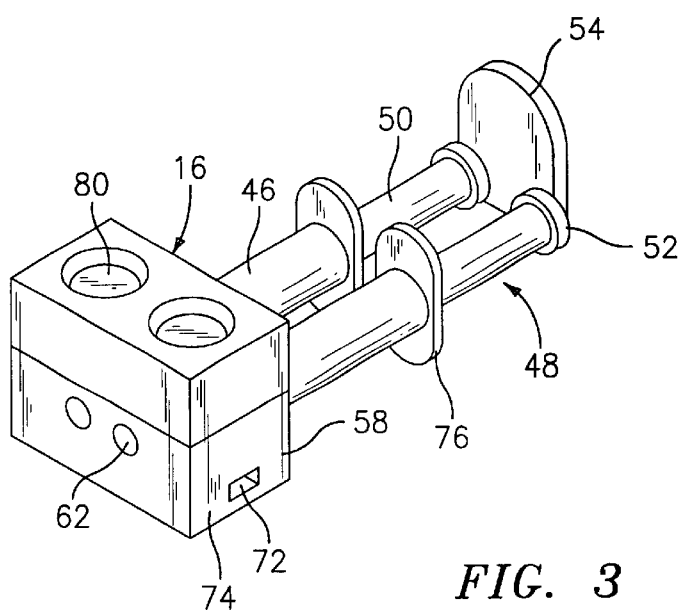
FIG. 3 is a perspective view of a disposable loading unit (DLU) having a coupler interface attached thereto.

The DLU 14 includes two piston assemblies 44 each having a cylinder 46, a piston 48 having a rod 50 connected to a stopper 52 at a proximal end. As shown by FIG. 3, a loading lever 54 connects each stopper 52 to one another to effect simultaneous movement of each rod 50 when the loading lever 54 is translated proximally to transfer the solutions from the vials 56 to the cylinders 46 as described below.

Figure 4A:
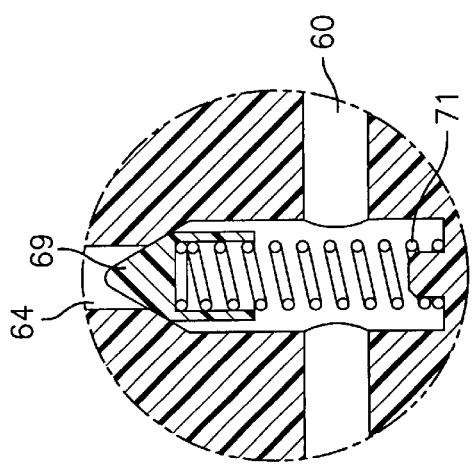
FIG. 4A is enlarged view of the one-way loading valve shown in FIG. 4.
Figure 4:
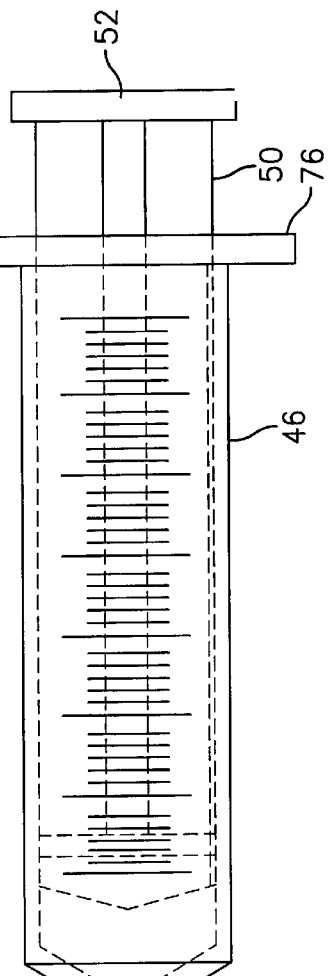
FIG. 4 is an enlarged cross-sectional view of the DLU and coupler interface with the one-way dispensing and one-way loading valves being in the closed position.
Figure 4:
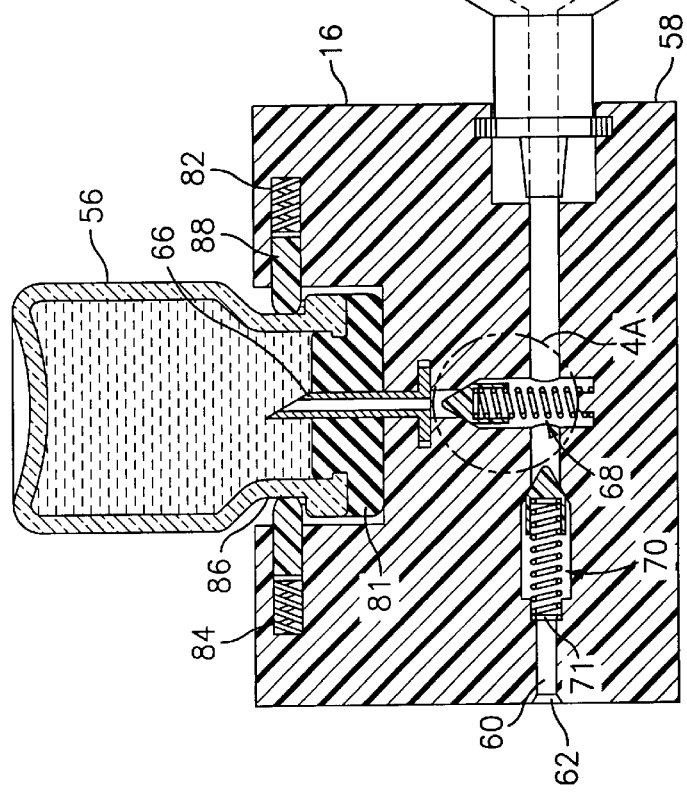

The DLU 14 further includes a dispensing unit 58 having two main conduits 60 therein each in fluid communication with a corresponding cylinder 46 at a proximal end and a dispensing orifice 62 at a distal end as shown by the cross-sectional view of FIG. 4. The dispensing unit 58 further includes two conduits 64 perpendicular to the two main conduits 60. The two conduits 64 are in fluid communication with a corresponding piercer 66 and a corresponding main conduit 60.

With reference to FIG. 3, the coupler interface 16 includes two holes 80 for receiving the vials 56 containing solutions of fibrinogen and thrombin which form a fibrin sealant when intermixed on an application site. Each piercer 66 of the dispensing unit 58 aligns with a corresponding hole 80 for piercing the protective seal 81 on each vial 56 when the vial 56 is inserted within the hole 80. As noted above each piercer 66 is in fluid communication with a conduit 64 connected to one of the main conduits 60 within the dispensing unit 58 for transferring the fibrinogen and thrombin solutions to a corresponding cylinder 46.

A one-way loading valve 68 is included within each conduit 64 which opens when the loading lever 54 is moved proximally as described below with reference to FIGS. 4B and 4C. A one-way dispensing valve 70 is included within each main conduit 60 which opens when the trigger 22 is pressed as described below with reference to FIGS. 5 and 6.

As shown by FIGS. 4 and 4A, each one-way valve includes a pointed tip 69 attached to a spring 71. The pointed tip 69 engages a mouth 73 of a conduit to prevent fluid flow in a first position and the pointed tip 69 disengages the mouth 73 of the conduit to permit fluid flow in a second position. The pointed tip 69 disengages the mouth 73 of the conduit when pressure is applied within the conduit by either translating the pistons 48 proximally to open the loading one-way valves 68 or distally to open the dispensing one-way valves 70 as described below with reference to FIGS. 4B to 5. The loading and dispensing one-way valves are both closed when the loading lever 54 is stationary or the trigger 22 is in the inactivated position.

Two notches 72 are included on two opposing faces 74 of the dispensing unit 58 which are used to snap-fit the dispensing unit 58 with the flanges 32 of the elongated body portion 18 to secure the DLU 14 to the housing 12. The DLU 14 is further secured to the housing 12 by two tabs 76 which are fitted around each piston rod 50 and are adapted to be press-fitted to the slot 34 on the flat surface 28 of the elongated body portion 18. In addition, a portion of the rods 50 and stoppers 52 of the pistons 48 are positioned within the two apertures 38 and slot 40 of the slide bar 36 to further secure the DLU 14 to the housing 12.

As shown by the cross-sectional view of FIG. 4, a spring mechanism 82 is included in proximity to each hole 80 of the coupler interface 16. The spring mechanism 82 includes two springs 84 and detents 88 attached thereto at opposing sides of the coupler interface 16 and equidistant from the piercer 66 for engaging the neck 86 of the vial 56 for locking and holding the vial 56 in position. It is contemplated to provide a safety door mechanism in proximity to each piercer 66 which would include safety doors which close above each piercer 66 when the vials 56 are removed from the coupler interface 16 to prevent the user from being accidentally pierced by the piercers 66.

The operation of the applicator system 10 will now be described with reference to FIGS. 4B to 6. As shown by FIG. 4B, the vial 56 is placed within the hole 80 to pierce the protective seal 81 by the piercer 66. The piston 48 is then translated proximally to create proximal air pressure from the tip of the piercer 66 to the interior of the cylinder 46, thereby disengaging the pointed tip 69 of the loading one-way valve 68 from the mouth 73 of the conduit 64 to transfer the protein solution within the cylinder 46. The enlarged view of FIG. 4C illustrates the disengagement of the pointed tip 69 of the loading one-way valve 68 from the mouth 73 of the conduit 64 as air pressure is created within the conduit 64. It is noted that both protein solutions are simultaneously transferred from their respective vial 56 to a corresponding cylinder 46 as the pistons 48 are simultaneously translated proximally.

Once the protein solutions have been transferred to their corresponding cylinders 46, the loading lever 54, the vials 56, and the coupler interface 16 can be removed from the DLU 14. The DLU 14 is then secured to the housing 12 as discussed above. The user can then bring the housing 12 with the DLU 14 attached thereto in proximity to a surgery site or a wound for dispensing the solutions to form a fibrin sealant over the surgery site or wound.

Figure 5:
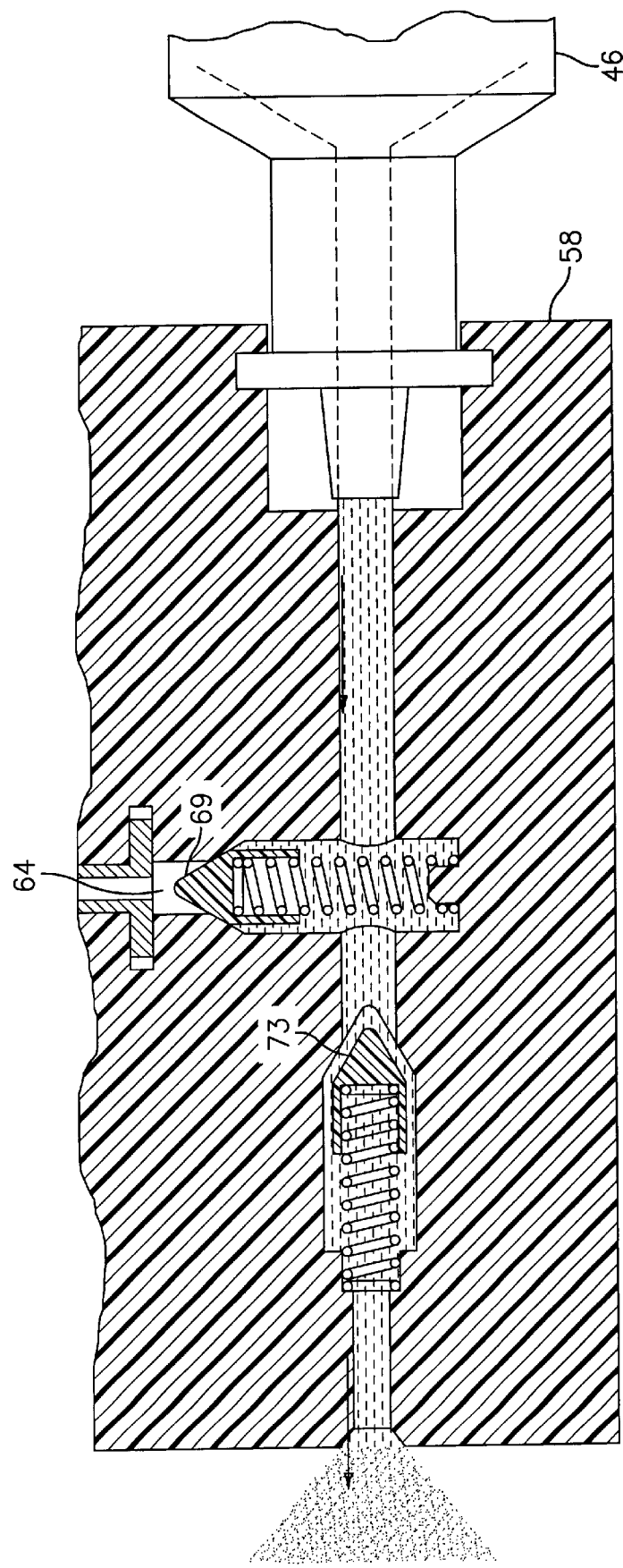
FIG. 5 is an enlarged cross-sectional view of the distal end of the applicator system showing the dispensing valve in the open position and the loading valve in the closed position for dispensing the protein solution.
Figure 6:
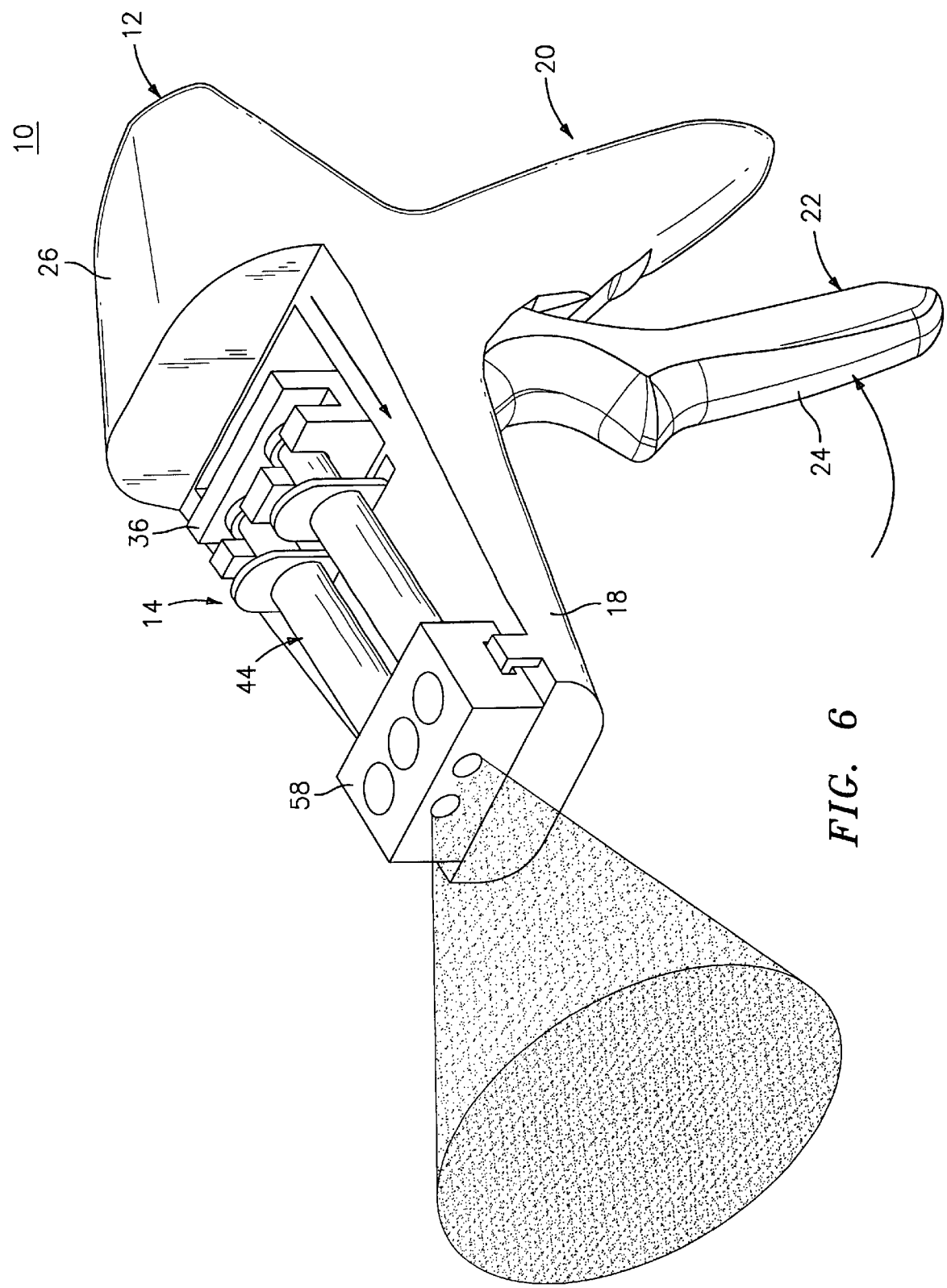
FIG. 6 is a perspective view showing the protein solutions being dispensed from the fibrin glue applicator system of FIG. 1 as the trigger is depressed.

The protein solutions are dispensed simultaneously as the trigger 22 is pressed by the user's fingers to cause the slide bar 36 to translate distally thereby forcing the pistons 48 to translate within the cylinders 46 to force the solutions to be dispensed within the main conduits 60. As each solution is dispensed within one of the main conduits 60, pressure is created upon the pointed tip 69 of each dispensing one-way valve 70 causing the pointed tip 69 to be disengaged from the mouth 73 of each main conduit 60 as shown by FIG. 5 to permit each solution to be dispensed from its respective dispensing orifice 62 as shown by FIG. 6.

It is contemplated that the present invention may be packaged as a kit for applying a solution of fibrinogen and a solution of thrombin on a wound to stop bleeding or the like. The kit may include the housing 12, the DLU 14, the coupler interface 16, and the dispensing unit 58.

It is understood that various modifications may be made to the embodiments disclosed herein. Also, besides applying solutions of fibrinogen and thrombin to form a fibrin sealant, the fibrin glue applicator system can be used to perform human or veterinary surgical procedures including applying antiseptics, medication and other similar procedures. Therefore, the above description should not be construed as limiting, but merely as exemplifications of preferred embodiments.

What is claimed is:

1. An applicator system for dispensing at least two components for forming a multicomponent biological adhesive, the applicator system comprising:
   a housing configured to receive a loading unit having at least two piston assemblies, each of said at least two piston assemblies having a piston matingly engaging a cylinder configured for retaining one of said at least two components;
   a dispensing unit having at least two conduits in fluid communication with the at least two piston assemblies, said dispensing unit configured to receive a coupler interface having at least two piercers in fluid communication with the at least two conduits; and
   an actuactor assembly provided on said housing having an activator moveable from a first position to a second position to compress each of said at least two pistons to dispense said at least two components through said at least two conduits in said dispensing unit.

2. The applicator system according to claim 1, wherein said coupler interface is configured for receiving two vials each storing one of said at least two components and wherein proximal translation of each piston causes a valve in proximity to each of said at least two piercers to move from a closed position to an open position for transferring said at least two components from said vials to said cylinders.

3. The applicator system according to claim 1, wherein said dispensing unit includes a valve within each of said at least two conduits configured to move from a closed position to an open position when said activator is moved from said first position to said second position.

4. An applicator system for dispensing at least two components for forming a multicomponent biological adhesive, the applicator system comprising:
   a housing configured to receive a loading unit having at least two piston assemblies configured for retaining said at least two components;
   a coupler interface having at least two piercers, said coupler interface configured to receive at least two vials each having a sealable opening and storing one of said at least two components;
   a conduit assembly having a first pair of conduits in fluid communication with said at least two piercers and a pair of main conduits, said conduit assembly having a second pair of conduits in fluid communication with a pair of dispensing orifices and said pair of main conduits, said pair of main conduits being in fluid communication with said at least two piston assemblies; and
   an activator assembly provided on said housing having an activator moveable from a first position to a second position to compress each of said at least two piston assemblies to dispense said at least two components through said pair of main conduits, said second pair of conduits, and said pair of dispensing orifices.

5. The applicator system according to claim 4, wherein said conduit assembly is housed within a dispensing unit configured for mounting adjacent a distal end of said at least two piston assemblies.

6. The applicator system according to claim 4, wherein said conduit assembly includes a first valve within each of said first pair of conduits configured to move from a closed position to an open position for transferring said at least two components from said at least two vials through said first pair of conduits, through said at least two main conduits to said at least two piston assemblies.

7. The applicator system according to claim 6, wherein each of said at least two piston assemblies includes a piston matingly engaging a cylinder, said piston moveable from a first position to a second position for creating a force within each of said first pair of conduits for moving said first valve from said closed position to said open position.

8. The applicator system according to claim 4, wherein said conduit assembly includes a second valve within each of said second pair of conduits configured to move from a closed position to an open position for transferring said at least two components from said at least two piston assemblies through said at least two main conduits to said pair of dispensing orifices.

9. The applicator system according to claim 8, wherein each of said at least two piston assemblies includes a piston matingly engaging a cylinder, said piston moveable from a first position to a second position to compress each of said at least two piston assemblies for creating a force within each of said second pair of conduits for moving said second valve from said closed position to said open position.

10. The applicator system according to claim 4, wherein said activator assembly includes control structure for restricting said activator from returning to said first position after the activator is moved from said first position.

11. The applicator system according to claim 10, wherein said control structure includes a ratchet mechanism.

12. The applicator system according to claim 4, wherein one of said at least two components is a thrombin solution and another of said at least two components is a fibrinogen solution, whereby said multicomponent biological adhesive is a fibrin sealant.

13. A manually-operated applicator for dispensing a first and second component of a biological adhesive, the applicator comprising:
- a conduit assembly having a first pair of conduits and a first valve movable from a closed position to an open position;
- a piston assembly having a first cylinder containing the first component and a second cylinder containing the second component, the first cylinder being in communication with a first of said first pair of conduits and the second cylinder being in communication with a second of first said pair of conduits; and
- an activator assembly having an activator for imparting distal pressure to said first and second cylinders to effect dispensing of said first and second components to said first pair of conduits and move said first valve from said closed position to said open position.

14. The manually-operated applicator according to claim 13, further including a coupler interface in engagement with said conduit assembly and configured to receive at least two vials storing said first and second components for replenishing said first and second cylinders.

15. The manually-operated applicator according to claim 14, wherein said coupler interface further includes a pair of piercers in fluid communication with a second pair of conduits in said conduit assembly to effect transferring of said first and second components from said vials to said first and second cylinders upon imparting proximal pressure to said first and second cylinders.

16. The manually-operated applicator according to claim 15, wherein each of said second pair of conduits includes a second valve configured to move from a closed position to an open position upon imparting proximal pressure to said first and second cylinders.

17. The manually-operated applicator according to claim 13, wherein said first component is a thrombin solution and said second component is a fibrinogen solution, whereby said biological adhesive is a fibrin sealant.

18. A kit for dispensing a first and second component of a biological adhesive, the kit comprising:
- a loading unit having at least two piston assemblies, each of said at least two piston assemblies having a piston matingly engaging a cylinder configured for retaining one of said first and second components;
- a housing configured to receive said loading unit;
- a dispensing unit having at least two conduits in fluid communication with said cylinders;
- a coupler interface configured for receiving at least two vials storing said first and second components therein, said coupler interface having at least two piercers in fluid communication with said cylinders;
- said housing having an activator moveable from a first position to a second position to compress said cylinders to dispense said first and second components to said at least two conduits, and said loading unit having a loading lever moveable from a first position to a second position to transfer said first and second components from said vials to said cylinders to replenish said first and second components within said cylinders.

* * * * *